United States Patent
Zhang

(10) Patent No.: US 7,341,568 B2
(45) Date of Patent: Mar. 11, 2008

(54) METHOD AND DEVICE FOR DETERMINING BLOOD VOLUME DURING AN EXTRACORPOREAL BLOOD TREATMENT

(75) Inventor: Wei Zhang, Niederwerm (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 6 days.

(21) Appl. No.: 10/520,484

(22) PCT Filed: May 30, 2003

(86) PCT No.: PCT/EP03/05657
§ 371 (c)(1),
(2), (4) Date: Jun. 29, 2005

(87) PCT Pub. No.: WO2004/004804
PCT Pub. Date: Jan. 15, 2004

(65) Prior Publication Data
US 2006/0047193 A1    Mar. 2, 2006

(30) Foreign Application Priority Data
Jul. 6, 2002    (DE) .............................. 102 30 413

(51) Int. Cl.
*A61M 37/00*    (2006.01)
*C02F 35/14*    (2006.01)
*B01D 35/14*    (2006.01)
*B01D 24/00*    (2006.01)

(52) U.S. Cl. ...................... 604/4.01; 604/5.01; 422/44; 422/45; 210/645; 210/646; 73/861.27

(58) Field of Classification Search ...... 604/4.01–6.16; 210/600, 321.6, 739–744, 645–647; 261/127–159; 600/301, 504, 507; 422/44–48; 73/1.16, 73/1.73, 149, 861, 861.18, 861.27–31
See application file for complete search history.

(56) References Cited

U.S. PATENT DOCUMENTS

| | | | | |
|---|---|---|---|---|
| 5,293,874 A * | 3/1994 | Takahashi et al. ........... 600/500 |
| 6,126,831 A * | 10/2000 | Goldau et al. ............... 210/646 |
| 6,217,539 B1 * | 4/2001 | Goldau ....................... 604/4.01 |
| 6,527,728 B2 * | 3/2003 | Zhang ......................... 600/500 |
| 6,623,443 B1 * | 9/2003 | Polaschegg ................ 604/5.04 |
| 6,736,789 B1 * | 5/2004 | Spickermann ............. 604/5.01 |

(Continued)

FOREIGN PATENT DOCUMENTS

DE    40 24 434    2/1992

(Continued)

*Primary Examiner*—Loan H. Thanh
*Assistant Examiner*—Phil Wiest
(74) *Attorney, Agent, or Firm*—Kenyon & Kenyon LLP

(57) ABSTRACT

The invention relates to a method for determining blood volume during extracorporeal blood circulation, which is based on measuring the propagation rate or propagation time of the pulse waves propagating in the extracorporeal circulation system. The invention preferably involves the measurement of the propagation rate or propagation time of the pulse waves generated by the blood pump, which is placed in arterial branch of the blood line. The device for determining blood volume can make use of the pressure sensor, which is placed in the venous branch of the blood line and which is already provided in prior art blood treatment devices. As a result, the amount of equipment required is relatively low.

18 Claims, 2 Drawing Sheets

U.S. PATENT DOCUMENTS 6,966,979 B2 * 11/2005 Pedrazzi ...................... 210/85
7,077,819 B1 * 7/2006 Goldau et al. ............. 604/5.04

FOREIGN PATENT DOCUMENTS

| DE | 197 46 377 | 7/1999 |
| DE | 100 51 943 | 5/2002 |
| EP | 0 358 873 | 3/1990 |
| EP | 0 911 044 | * 4/1999 |

* cited by examiner

METHOD AND DEVICE FOR DETERMINING BLOOD VOLUME DURING AN EXTRACORPOREAL BLOOD TREATMENT

FIELD OF THE INVENTION

The invention relates to a method for the determination of the blood volume during an extracorporeal blood treatment with a blood treatment apparatus in an extracorporeal blood circuit as well as a device for the determination of the blood volume during an extracorporeal blood treatment.

BACKGROUND OF THE INVENTION

For the purpose of removing substances usually eliminated with urine and for the purpose of withdrawing fluid, use is made of various methods for machine-aided blood cleaning or blood treatment in acute or chronic kidney failure. Diffusive substance transport predominates in the case of haemodialysis (HD), whilst convective substance transport via the membrane takes place in the case of haemofiltration (HF). Haemodiafiltration (HDF) is a combination of the two methods.

During extracorporeal blood treatment, the patient's blood flows via an arterial branch of a tube-line system into a blood treatment apparatus, for example a haemodialyser or haemofilter, and flows from the blood treatment apparatus via a venous branch of the line system back to the patient. The blood is conveyed by means of a blood pump, in particular a roller pump, which is arranged in the arterial branch of the line system. Fluid can be withdrawn from the patient during the extracorporeal treatment (ultrafiltration).

One of the main complications with extracorporeal blood treatment is an acute drop in blood pressure (hypotony), which can be caused by an excessively high or rapid fluid withdrawal. There are various solutions to this problem. On the one hand, blood pressure monitors are known which continuously monitor a change in the blood pressure and regulate the ultrafiltration in dependence on the change in blood pressure. On the other hand, blood volume monitors are known which measure the relative blood volume during the dialysis treatment and carry out a regulation of the ultrafiltration in dependence on the relative blood volume.

DE-C-197 46 377 describes a device for measuring blood pressure, which is based on the detection of the propagation rate or transit time of the pulse waves being propagated via the arterial vessel system of the patient, said pulse waves being generated by the patient's heart contractions.

There is known from DE-A-40 24 434 a device for the regulation of ultrafiltration, in which the pressure in the extracorporeal circuit is monitored in order to determine the relative blood volume. The change in the blood volume is deduced from the change in the pressure in the course of the blood treatment compared with the pressure at the start of the treatment.

There is known from DE 100 51 943 A1 a method for the non-invasive blood pressure measurement of patients on the basis of pulse-wave transit times during an extracorporeal blood treatment.

SUMMARY OF THE INVENTION

An object of the invention is to provide a method which permits the determination of the blood volume during an extracorporeal blood treatment without major expenditure on equipment. A further object of the invention is to provide a device which enables the determination of the blood volume during an extracorporeal blood treatment without major expenditure on equipment.

The method according to the invention and the device according to the invention are based on the generation of pulse waves in the extracorporeal blood circuit, whereby the propagation rate or transit time of the pulse waves being propagated in the extracorporeal circuit is measured. The blood volume is determined from the measured propagation rate or transit time of the pulse waves.

The blood volume can be determined from the propagation rate or transit time of the pulse waves, because certain blood constituents, e.g. haemoglobin, proteins etc., remain in the extracorporeal blood circuit, but the plasma water is removed. Changes in the concentration of the blood constituents can thus be used to measure the change in the blood volume.

When mention is made of blood volume in the following, this is understood to mean both the absolute as well as the relative blood volume. The relative blood volume at time t is defined by:

$$RBV(t) = \frac{V(t)}{V(0)} \qquad (1)$$

whereby

V(0) is the blood volume at time t=0, i.e. at the start of the dialysis treatment, and V(t) is the blood volume at time t, i.e. in the course of treatment.

Since the method according to the invention and the device according to the invention make use of the pressure measurement that is anyhow present in the known dialysis machines, the outlay on equipment is relatively small. A suitable expansion of the software for the microprocessor control of the machine is solely required for the determination of the blood volume.

In a preferred embodiment of the invention, the propagation rate or transit time of the pressure pulse-waves is measured in the extracorporeal circuit, said pressure pulse-waves being caused by the blood pump which is arranged in the extracorporeal circuit of the known haemodialysis machines. The blood pump of the known dialysis machines is generally a roller pump, which generates pressure pulses with each rotation of the pump rotor.

The pulse waves generated by the blood pump are preferably detected by a pressure sensor, which is arranged in the extracorporeal circuit with known dialysis machines.

In order to increase the accuracy, the pressure measurement can be carried out to advantage with a pressure sensor which is arranged without an air column in direct contact on the blood tube or on a pressure-measuring chamber provided before the latter, through which the blood line runs.

In a particularly preferred embodiment of the invention, the blood pump is arranged in the arterial branch of the blood line upstream of the blood treatment apparatus and the pressure sensor for detecting the pulse waves downstream of the blood treatment apparatus in the venous branch of the blood line. The section over which the transit time is to be measured is thus the part of the blood line lying between blood pump and pressure sensor.

If the time at which the pulse waves are generated by the blood pump is not known, the pulse waves generated by the blood pump can be detected with a second pressure sensor which is arranged upstream of the blood treatment apparatus in the arterial branch of the blood line. The time can however also be derived from the position of the pump rotor, which is detected for example by a Hall sensor. The Hall sensor can have a magnet rotating with the rotor, the magnetic field whereof periodically penetrates a Hall probe located on the stator, a suitable electrical voltage signal being able to be picked up at said Hall probe.

A further embodiment of the invention provides for the determination of the relative blood volume from the ratio of the propagation rates or transit times of the pulse waves at two different times in the blood treatment, in particular at the start and during the course of the treatment.

DETAILED DESCRIPTION

Figure 1:
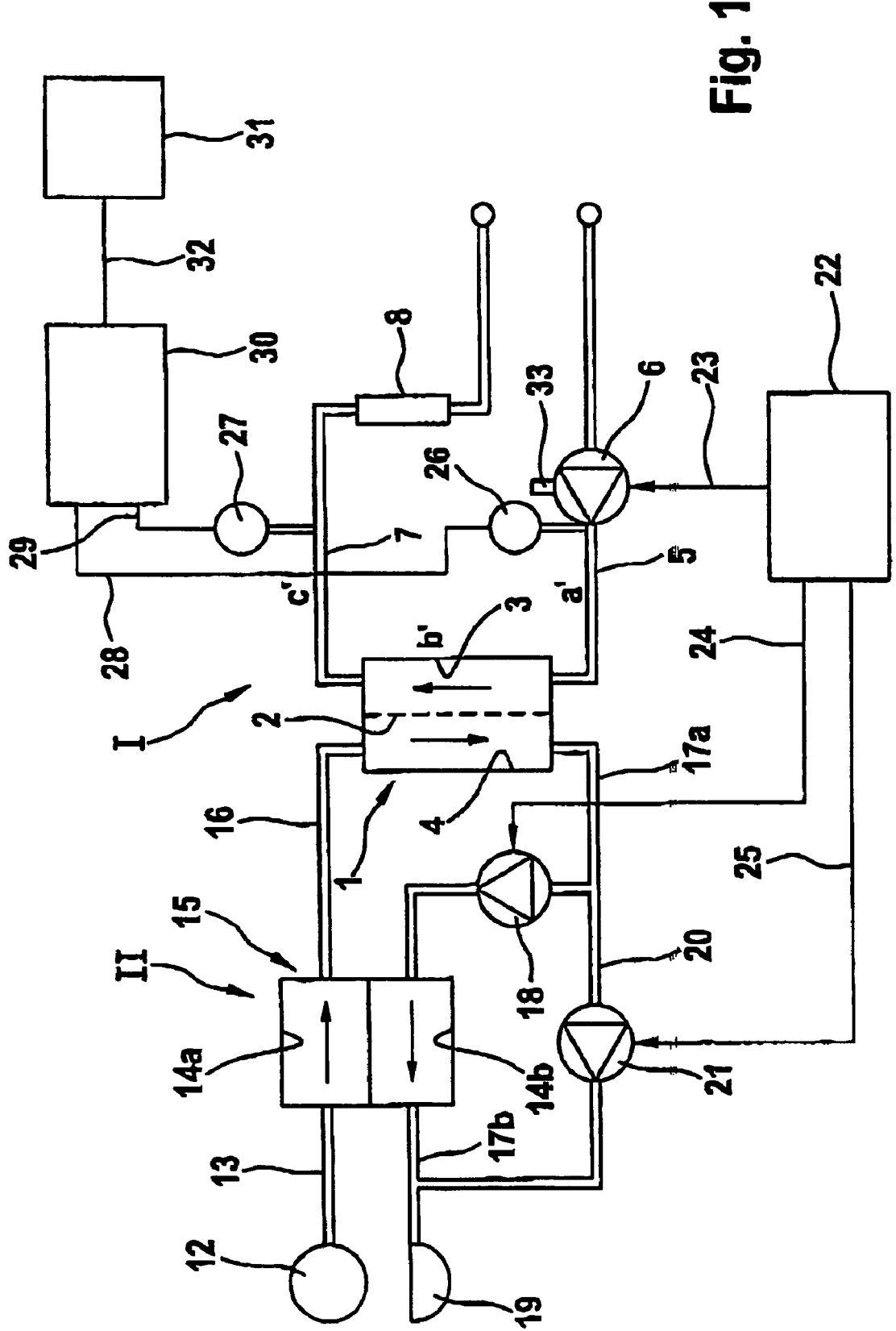
FIG. 1 is a very simplified diagrammatic representation of the essential components of a dialysis machine with a device for determining the relative blood volume.

An exemplary embodiment of a dialysis machine with a device for determining the relative blood volume is explained in greater detail below with the aid of the drawings.

The haemodialysis apparatus has a dialyser 1, which is divided by a semipermeable membrane 2 into a blood chamber 3 and a dialysing fluid chamber 4. The inlet of the blood chamber is connected to one end of an arterial blood feed line 5, into which an arterial blood pump 6 is incorporated, whilst the outlet of blood chamber 3 is connected to one end of venous blood discharge line 7, into which a drip chamber 8 is incorporated. Blood feed line and blood discharge line 5, 7 are conventional tube lines, which form the arterial and venous branch respectively of extracorporeal circuit I.

Blood pump 6 is a conventional roller pump, which with each rotation generates two pressure pulses which are propagated via blood feed line 5, blood chamber 3 and blood discharge line 7 in extracorporeal blood circuit I. The pressure waves are generated whenever the rotor of roller pump 6 occupies a certain position. In order to monitor the position of the pump rotor, roller pump 6 has a Hall sensor 33. Dialysing fluid system II of the haemodialysis machine comprises a device 12 for preparing the dialysing fluid, which is connected by a first section 13 of a dialysing fluid feed line to the inlet of first chamber half 14a of a balancing device 15. Second section 16 of the dialysing fluid feed line connects the outlet of first balancing chamber half 14a to the inlet of dialysing fluid chamber 4. The outlet of dialysing fluid chamber 4 is connected via first section 17a of a dialysing fluid discharge line to the inlet of second balancing chamber half 14b. A dialysing fluid pump 18 is incorporated into first section 17a of the dialysing fluid discharge line. The outlet of second balancing chamber half 14b is connected via second section 17b of the dialysing fluid discharge line to a discharge 19. An ultra-filtrate line 20, which also leads to discharge 19, branches off from dialysing fluid discharge line 17a upstream of dialysing fluid pump 18. An ultrafiltration pump 21 is incorporated into ultra-filtrate line 20.

A second balancing chamber usually present, which is operated in parallel and phrase-shifted with respect to the first balancing chamber in order to guarantee a virtually constant flow, is not shown in FIG. 1 for the sake of simplicity.

The haemodialysis machine further comprises a central control unit 22, which is connected via control lines 23 to 25 to blood pump 6, dialysing fluid pump 18 and ultrafiltration pump 21.

During the haemodialysis treatment, the patient's blood flows through the blood chamber and the dialysing fluid flows through the dialysing fluid chamber of the dialyser. Since balancing device 15 is incorporated into the dialysing fluid path, only as much dialysing fluid can flow in via dialysing fluid feed line as dialysing fluid can flow away via dialysing fluid discharge line. Fluid can be withdrawn from the patient with ultrafiltration pump 21.

The haemodialysis machine also has a device for the non-invasive determination of the relative blood volume during the dialysis treatment. This device makes use of various components of the haemodialysis machine. It is therefore part of the dialysis machine. The device for determining the relative blood volume will be described in detail below.

The device for determining the relative blood volume has a pressure sensor 26 for measuring the pressure in blood feed line 5 downstream of blood pump 6 and upstream of blood chamber 3 of dialyser 1 and a pressure sensor 27 for measuring the pressure in blood discharge line 7 downstream of blood chamber 3 of the dialyser. Both pressure sensors 26, 27 are connected via signal lines 28, 29 to an analysing unit 30, in which the signals of the sensors are processed. This analysing unit is a component of the microprocessor control of the haemodialysis machine. From the measured pressure values, the analysing unit determines the relative blood volume, which is displayed on a display unit 31 which is connected via a data line 32 to the analysing unit.

The functioning of the device for determining the relative blood volume RBV will be described as follows. The determination of the relative blood volume is based on the measurement of the transit time of the pulse waves generated by blood pump 6 which are propagated in extracorporeal blood circuit I. Measurement section L consists of the parts of the blood line and the blood chamber between arterial and venous pressure sensors 26, 27. This section L is indicated in FIG. 1 by a', b' and c'.

The theoretical relationship between the pulse-wave transit time and the RBV is derived as follows. In an incompressible fluid, which is present in an elastic cylindrical tube with cross-sectional area A, the propagation rate c of a longitudinal pressure wave is given by:

$$c = \sqrt{\frac{A\,dp}{\rho\,dA}} \qquad (2)$$

whereby
  c pulse wave speed
  $\rho$ density of the fluid
  dp change in pressure
  dA change in area During the dialysis treatment, transit time PTT ("pulse transit time") over the part of the blood tube system (measurement section) with total length L between the arterial pressure sensor preferably arranged directly downstream of the blood pump, or more precisely the blood pump, and the venous pressure sensor amounts to:

$$PTT = \frac{L}{c} = L\sqrt{\frac{\rho}{A} \cdot \frac{dA}{dp}} \quad (3)$$

From equation (3) we have:

$$PTT(t_0) = L\sqrt{\rho(t_0)\left(\frac{dA/A(t_0)}{dp}\right)_{t_0}} \quad (4)$$

$$PTT(t) = L\sqrt{\rho(t)\left(\frac{dA/A(t)}{dp}\right)_t} \quad (5)$$

whereby
PTT($t_0$) transit time at time $t_0$
PTT(t) transit time at time t
With equation (4) and (5), we obtain:

$$\frac{PTT(t)}{PTT(t_0)} = \sqrt{\frac{\rho(t)\left(\frac{dA/A(t)}{dp}\right)_t}{\rho(t_0)\left(\frac{dA/A(t_0)}{dp}\right)_{t_0}}} \quad (6)$$

$$\left(\frac{PTT(t)}{PTT(t_0)}\right)^2 = \frac{\rho(t)}{\rho(t_0)} K(P) \quad (7)$$

$$K(P) = \left(\frac{dA/A(t)}{dp}\right)_t \bigg/ \left(\frac{dA/A(t_0)}{dp}\right)_{t_0} \quad (8)$$

Here, K(P) denotes the ratio of the expansion size of the tube at time t and $t_0$ The mass density of the blood is defined by the ratio of the mass fraction of the protein and water in the blood to the total blood volume by:

$$\rho(t_0) = \frac{m_{protein}(t_0) + m_{water}(t_0)}{V(t_0)} \quad (9)$$

$$\rho(t) = \frac{m_{protein}(t) + m_{water}(t)}{V(t)} \quad (10)$$

whereby
$\rho(t_0)$ mass; density of blood at time $t_0$
$\rho(t)$ mass density of blood at time t
$V(t_0)$ blood volume at time $t_0$
V(t) blood volume at time t
$m_{protein}(t_0)$ mass of proteins in V ($t_0$) at time $t_0$
$m_{protein}(t)$ mass of proteins in V ($t_0$) at time t
$m_{water}(t_0)$ mass of water in V ($t_0$) at time $t_0$
$m_{water}(t)$ mass of water in V ($t_0$) at time t Since the membrane of a dialyser is not permeable for the majority of the blood proteins, the blood protein content during haemodialysis remains approximately constant, i.e. $m_{protein}(t) = m_{protein}(t_0)$. From equation (9), (10) and (1), we have:

$$\frac{\rho(t)}{\rho(t_0)} = \frac{1}{RBV(t)}\left(1 - \frac{m_{water}(t_0) - m_{water}(t)}{m_{protein}(t_0) + m_{water}(t_0)}\right) \quad (11)$$

With $m_{water}(t_0) - m_{water}(t) = V(t_0) \cdot [1 - RBV(t)] \cdot \rho_w$, equation (11) can be written in the form $$\frac{\rho(t)}{\rho(t_0)} = \frac{1}{RBV(t)}\left(1 - \frac{\rho_w}{\rho(t_0)} + RBV(t)\frac{\rho_w}{\rho(t_0)}\right) \quad (12)$$

Whereby $\rho_w$ denotes the mass density of water.
With equation (7) and (12), we obtain $$\left(\frac{PTT(t)}{PTT(t_0)}\right)^2 = \frac{1}{RBV(t)}\left(1 - \frac{\rho_w}{\rho(t_0)} + RBV(t)\frac{\rho_w}{\rho(t_0)}\right)K(P) \quad (13)$$

The solution to this equation reads as follows:

$$RBV(t) = \frac{\left(1 - \frac{\rho_w}{\rho(t_0)}\right)K(P)}{\left(\frac{PTT(t)}{PTT(t_0)}\right)^2 - \frac{\rho_w}{\rho(t_0)}K(P)} \quad (14)$$

If the tube system is elastic and remains within the proportionality range (elasticity range) during the treatment, K(P)=1 according to Hooke's law. From this we have:

$$RBV(t) = \frac{1 - \frac{\rho_w}{\rho(t_0)}}{\left(\frac{PTT(t)}{PTT(t_0)}\right)^2 - \frac{\rho_w}{\rho(t_0)}} \quad (15)$$

Equation (15) shows that the relative blood volume RBV (t) is a function of the ratio of the transit times and the blood density at time $t_0$. On the assumption that the blood density prior to the dialysis treatment is approximately the same for all patients, RBV(t) depends solely on the ratio of the transit times.

If, however, the elasticity of the tube depends on the pressure in the tube, in particular if there is a non-linear relationship between the elasticity and the pressure, a characteristic curve can be used for K(P).

At the start of the dialysis treatment, analysing unit 30 determines transit time PTT($t_0$) at time $t_0$. This value is stored in a memory. The values for the mass density $\rho_w$ of water and the density $\rho(t_0)$ of blood at the start of the dialysis treatment are also inputted into this memory. These values are taken as constants. They can be inputted externally or permanently preset.

In order to determine transit time PTT($t_0$), a measurement is made of the time that a pulse wave requires in order to travel from arterial pressure sensor 26 to venous pressure sensor 27.

Even if the measurement section a'+b'+c' in FIG. 1 permits a long measuring time, it needs to be taken into account that elements with different elasticity are present along this section. Thus, for example, the dialyser and blood tube have different properties with respect to elasticity. In order to avoid disturbing influences, therefore, measurements can only be made over a measurement section along the blood tube upstream or downstream of the dialyser. Either an arterial pressure sensor for measuring the transit time between the pump and the arterial pressure sensor should then be provided downstream of the blood pump or two venous pressure sensors should be provided for measuring the transit time between the two venous sensors.

Figure 2:
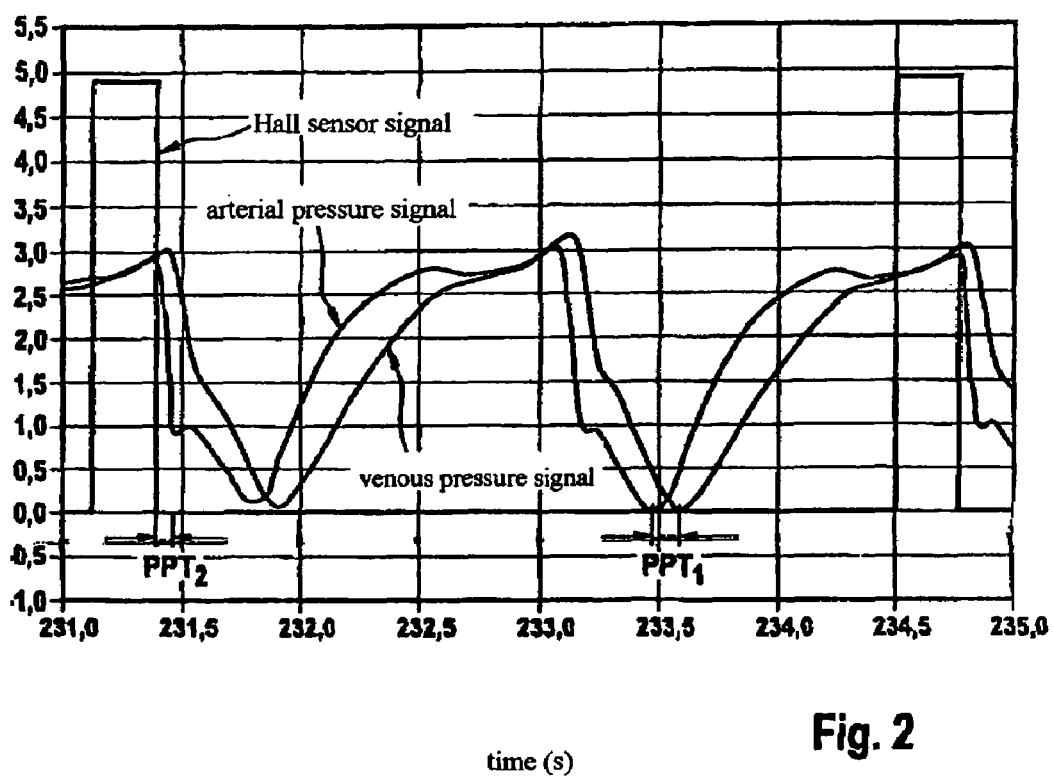
FIG. 2 shows the temporal course of the signals of an arterial and venous pressure sensor for determining the pressure in the arterial and venous branch of the blood line and the signal of a Hall sensor for determining the position of the pump rotor.

FIG. 2 shows the temporal course of the pressure signals of pressure sensors 26, 27. It can clearly be seen that the pulse wave arrives first at the arterial and then at the venous pressure sensor. The transit time over measurement section L between arterial and venous pressure sensor is denoted in FIG. 2 by $PTT_1$. In order to have a particularly long measurement section, arterial pressure sensor 26 should be arranged immediately downstream of blood pump 6 and venous pressure sensor 27 as far as possible downstream of blood chamber 3 in the blood line.

During the dialysis treatment, analysing unit 30 continuously determines transit time PTT(t) of the pulse waves and continuously calculates the relative blood volume RBV(t) according to equation (15).

On the assumption of a non-linear relationship between the elasticity and the pressure, a characteristic curve for K(p) is stored in the memory. The calculation of the relative blood volume then takes place according to equation (14).

An alternative embodiment of the invention provides only one venous pressure sensor 27 in blood discharge line 7. Arterial pressure sensor 26 in blood feed line 5 is in principle not required. In place of the arterial pressure sensor, the occurrence of the pressure waves can be detected with Hall sensor 33 of the blood pump.

FIG. 2 shows the Hall signal of sensor 33. It can clearly be seen that the negative flanks of the Hall and pressure signal coincide. The transit time over the section between the blood pump and the venous pressure sensor is denoted in FIG. 2 by $PTT_2$. Since the magnet on the rotor of the blood pump leads to only one signal pre revolution and the rotor has two occluding rollers, the Hall signal occurs only with half the frequency compared with the pressure signal.

The invention claimed is:

1. A method for the determination of a blood volume during an extracorporeal blood treatment with a blood treatment apparatus in an extracorporeal blood circuit, wherein the extracorporeal blood circuit includes an arterial branch of a blood line leading to the blood treatment apparatus and a venous branch of the blood line leading away from the blood treatment apparatus, the method comprising:
   generating pulse waves that originate in the extracorporeal blood circuit, wherein the pulse waves have at least one of a propagation rate and a transit time;
   measuring the at least one of the propagation rate and the transit time of the pulse waves; and
   determining the blood volume from the at least one of the measured propagation rate and the measured transit time of the pulse waves.

2. The method of claim 1, wherein the pulse waves are generated by a blood pump arranged in the extracorporeal blood circuit.

3. The method of claim 2, further comprising:
   detecting the pulse waves by a first pressure sensor arranged in the extracorporeal blood circuit.

4. The method of claim 3, wherein the blood pump is arranged in the arterial branch of the blood line upstream of the blood treatment apparatus, and the first pressure sensor is arranged in the venous branch of the blood line downstream of the blood treatment apparatus.

5. The method of claim 4, further comprising:
   detecting the pulse waves by a second pressure sensor, wherein the second pressure sensor is arranged in the arterial branch of the blood line upstream of the blood treatment apparatus.

6. The method of claim 1, wherein determining the blood volume comprises determining a relative blood volume RBV(t) from a ratio of the at least one of the measured propagation rates and the measured transit times of the pulse waves at two different times t, $t_0$ of the extracorporeal blood treatment.

7. The method of claim 5, wherein determining the blood volume comprises determining a relative blood volume RBV(t) from a ratio of the at least one of the measured propagation rates and the measured transit times of the pulse waves at two different times t, $t_0$ of the extracorporeal blood treatment.

8. The method of claim 6, wherein the relative blood volume RBV(t) is calculated from the temporal change in the measured transit times of the pulse waves according to the following equation:

$$RBV(t) = \frac{1 - \frac{\rho_w}{\rho(t_0)}}{\left(\frac{PTT(t)}{PTT(t_0)}\right)^2 - \frac{\rho_w}{\rho(t_0)}}$$

wherein PTT(t) and PTT($t_0$) is the measured transit time of the pulse waves over a segment of the extracorporeal blood circuit with a predetermined length L at time t and $t_0$, respectively; and wherein $r_w$ is the mass density of water and $r(t_0)$ is the mass density of the blood at the start of the extracorporeal blood treatment.

9. The method of claim 7, wherein the relative blood volume RBV(t) is calculated from the temporal change in the measured transit times of the pulse waves according to the following equation:

$$RBV(t) = \frac{1 - \frac{\rho_w}{\rho(t_0)}}{\left(\frac{PTT(t)}{PTT(t_0)}\right)^2 - \frac{\rho_w}{\rho(t_0)}}$$

wherein PTT(t) and PTT($t_0$) is the measured transit time of the pulse waves over a segment of the extracorporeal blood circuit with a predetermined length L at time t and $t_0$, respectively; and wherein $r_w$ is the mass density of water and $r(t_0)$ is the mass density of the blood at the start of the extracorporeal blood treatment.

10. A device for the determination of the blood volume during an extracorporeal blood treatment in an extracorporeal blood circuit, wherein the extracorporeal blood circuit includes an arterial branch of a blood line leading to a blood treatment apparatus and a venous branch of the blood line leading away from the blood treatment apparatus, the device comprising:
   means for generating pulse waves that originate in the extracorporeal blood circuit, wherein the pulse waves have at least one of a propagation rate and a transit time;

means for measuring the at least one of the propagation rate and the transit time of the pulse waves; and an analyzing unit configured to determine the blood volume from the at least one of the measured propagation rate and the measured transit time of the pulse waves.

11. The device of claim 10, wherein the means for generating pulse waves comprises a blood pump arranged in the extracorporeal blood circuit.

12. The device of claim 11, further comprising:

a first pressure sensor for detecting the pulse waves, wherein the first pressure sensor is arranged in the extracorporeal blood circuit.

13. The device of claim 12, wherein the blood pump is arranged in the arterial branch of the blood line upstream of the blood treatment apparatus, and the first pressure sensor is arranged in the venous branch of the blood line downstream of the blood treatment apparatus.

14. The device of claim 13, further comprising:

a second pressure sensor for detecting the pulse waves, wherein the second pressure sensor is arranged in the arterial branch of the blood line upstream of the blood treatment apparatus.

15. The device of claim 10, wherein the analyzing unit is adapted to determine a relative blood volume RBV(t) from a ratio of the at least one of the measured propagation rates and the measured transit times of the pulse waves at two different times t, $t_0$ of the extracorporeal blood treatment.

16. The device of claim 14, wherein the analyzing unit is adapted to determine a relative blood volume RBV(t) from a ratio of the at least one of the measured propagation rates and the measured transit times of the pulse waves at two different times t, $t_0$ of the extracorporeal blood treatment.

17. The device of claim 15, wherein the analyzing unit is adapted to calculate the relative blood volume RBV(t) from the temporal change in the measured transit times of the pulse waves according to the following equation:

$$RBV(t) = \frac{1 - \frac{\rho_w}{\rho(t_0)}}{\left(\frac{PTT(t)}{PTT(t_0)}\right)^2 - \frac{\rho_w}{\rho(t_0)}}$$

wherein PTT(t) and PTT($t_0$) is the measured transit time of the pulse waves over a segment of the extracorporeal blood circuit with a predetermined length L at time t and $t_0$, respectively; and wherein $r_w$ is the mass density of water and $r(t_0)$ is the mass density of the blood at the start of the extracorporeal blood treatment.

18. The device of claim 16, wherein the analyzing unit is adapted to calculate the relative blood volume RBV(t) from the temporal change in the measured transit times of the pulse waves according to the following equation:

$$RBV(t) = \frac{1 - \frac{\rho_w}{\rho(t_0)}}{\left(\frac{PTT(t)}{PTT(t_0)}\right)^2 - \frac{\rho_w}{\rho(t_0)}}$$

wherein PTT(t) and PTT($t_0$) is the measured transit time of the pulse waves over a segment of the extracorporeal blood circuit with a predetermined length L at time t and $t_0$, respectively; and wherein $r_w$ is the mass density of water and $r(t_0)$ is the mass density of the blood at the start of the extracorporeal blood treatment.

* * * * *